United States Patent
Blizzard et al.

(10) Patent No.: US 9,273,194 B1
(45) Date of Patent: Mar. 1, 2016

(54) COMPOSITIONS HAVING SURFACTANT AND ADHESION PROPERTIES

(71) Applicants: John D. Blizzard, Bay City, MI (US); Robert L. McKellar, Midland, MI (US)

(72) Inventors: John D. Blizzard, Bay City, MI (US); Robert L. McKellar, Midland, MI (US)

( * ) Notice: Subject to any disclaimer, the term of this patent is extended or adjusted under 35 U.S.C. 154(b) by 0 days.

(21) Appl. No.: 14/506,742

(22) Filed: Oct. 6, 2014

(51) Int. Cl.
- *C07F 7/10* (2006.01)
- *C08K 5/5419* (2006.01)
- *C08K 3/40* (2006.01)
- *C09J 183/08* (2006.01)

(52) U.S. Cl.
CPC .................. *C08K 5/5419* (2013.01); *C08K 3/40* (2013.01); *C07F 7/10* (2013.01); *C09J 183/08* (2013.01)

(58) Field of Classification Search
CPC .................................. C07F 7/10; C09J 183/08
See application file for complete search history.

(56) References Cited

U.S. PATENT DOCUMENTS

| | | | | |
|---|---|---|---|---|
| 4,035,411 | A * | 7/1977 | Heckert et al. | 556/413 |
| 6,395,856 | B1 * | 5/2002 | Petty et al. | 528/24 |
| 6,395,858 | B1 * | 5/2002 | Mack et al. | 528/38 |
| 6,605,683 | B1 * | 8/2003 | Zhang | 528/14 |
| 2007/0036906 | A1 * | 2/2007 | Reeve | 427/421.1 |
| 2010/0104650 | A1 * | 4/2010 | Lee et al. | 424/489 |
| 2011/0143149 | A1 * | 6/2011 | Shibayama et al. | 428/447 |
| 2014/0208981 | A1 * | 7/2014 | Standke et al. | 106/287.11 |

* cited by examiner

*Primary Examiner* — Margaret Moore

(57) ABSTRACT

A composition of matter that has surfactant properties in aqueous solutions. The presence of a large number of silanols on the molecules of these compositions creates a solubility or disperseability of these molecules in aqueous solutions that is not obtainable from the quaternary salt monomers. The compositions also have adhesive properties when cured with or without functional organic materials.

11 Claims, No Drawings

COMPOSITIONS HAVING SURFACTANT AND ADHESION PROPERTIES

BACKGROUND OF THE INVENTION

This invention deals with compositions of matter that have surfactant properties in aqueous solutions and adhesion properties when cured, including co-curing with reactive organic compounds. The presence of a large number of silanols on the molecules of this invention creates a solubility or disperseability of these molecules in aqueous solutions that is not obtainable from the quaternary salt monomers per se. These materials, when cured, have very good adhesion to solid substrates, and when cured with reactive organic molecules, provide adhesion to solid substrates. It should be noted that these molecules provide very good adhesive properties to bond various solid substrates to each other. The inventors herein are not aware of any like molecules in the prior art.

THE INVENTION

Thus, what is disclosed and claimed herein is a composition of matter having the average general formula:

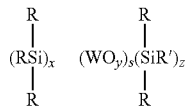

wherein the average molar ratio of x:y:z is 0.25–3:4:0.25–3, with the proviso that there is present at least one R'Si— unit and W is independently selected from the group consisting essentially of Si, Ti, and Zr, wherein R is independently selected from the group consisting essentially of hydroxyl radicals, alkyl groups of 1 to 8 carbon atoms, substituted alkyl groups of 1 to 8 carbon atoms, aryl groups, substituted aryl groups of 1 to 8 carbon atoms, y has a value of 4 and s has an average value of about 1 to 5.

R' is the group —$(R'')N^+(CH_3)_2$ $(R^v)Cl^-$, wherein R'' is an alkylene radical of three to six carbon atoms, $R^v$ is an alkyl radical of 10 to 22 carbon atoms, wherein $(WO_y)$ is derived from $W(OR''')_4$ wherein $(OR''')$ is independently selected from the group consisting of —$OCH_3$, —$OCH_2CH_3$, —$OCH(CH_3)_2$, —$O(CH_2)_3$ $CH_3$, —$OCH_2CH(CH_3)_2$, —$O(2$-ethylhexyl), acetoxy, and, oximo.

DETAILED DESCRIPTION OF THE INVENTION

One method for providing the materials of this invention comprises providing the components:

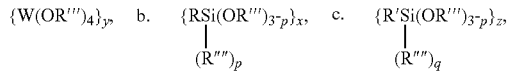

wherein the molar ratio of x:y:z is 0.25–3:4:0.25–3, $p$ and $q$ each independently have a value of 2 or less, R'''' is independently selected from the methyl group or the phenyl group, and co-hydrolyzing the components in the presence of a stoichiometric amount of water, and a catalyst for hydrolysis and condensation. The components $\{W(OR''')_4\}_y$, $\{RSi(OR''')3-p\}x$, and $\{R'Si(OR''')3-q\}z$ are commercially available from several sources.

By careful, controlled hydrolysis of the precursor monomers, one can obtain these materials at very low molecular weights providing a large number of silanols, the detail of which can be found infra in the specification, and in the examples. By "large number of silanols" it is meant that at least half of the Si atoms in the molecule are bonded by hydroxy groups.

The materials have the average general formula

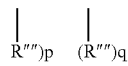

which is derived by the hydrolysis of the silane precursors

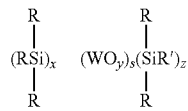

in conjunction with the orthosilicate, or orthotitanate, orthozirconate, or orthoaluminate having the general formula $\{W(OR''')_4\}_y$, wherein the molar ratio of x:y:z is 0.25–3:4:0.25–3.

This hydrolysis is carried out using a stoichiometric or near stoichiometric amounts of water and a catalyst for hydrolysis and condensation. Stoichiometric amounts of water, or, an amount of water greater than stoichiometric, results in low molecular weight materials, which is one of the objectives of the method of this invention.

It is believed by the inventors herein that the key to this invention is the use of the molecule $\{W(OR''')_4\}_y$ as the third component of this invention. W in the case of this invention is independently selected from the group consisting of Si, Ti, and Zr. Preferred for this invention is Si and Ti and most preferred is Si.

The (OR''') group is selected from the group consisting of —$OCH_3$, —$OCH_2CH_3$, —$OCH(CH_3)_2$, —$O(CH_2)_2$ $CH_3$, —$OCH_2CH(CH_3)_2$, —$O(2$-ethylhexyl), acetoxy, and, oximo. Preferred for this invention are the groups —$OCH_3$, —$OCH_2CH_3$, and —$OCH(CH_3)_2$, and most preferred are the —$OCH_3$ and —$OCH_2CH_3$ groups. Preferred orthosilicates and orthotitanates for this invention are Si $(OCH_2CH_3)_4$ and Ti $(—OCH(CH_3)_2)_4$.

Stoichiometry is based on the number of hydrolysable groups on the combined components. The reaction is carried out in the presence of base or acid, with acid being the preferred catalyst. The acid catalysts are preferred to be HCl, phosphoric, and acetic acids, with HCl and phosphoric acids being most preferred.

Bases that are useable herein are amines, NaOH, KOH and the like and preferred for this invention is NaOH. The hydrolysis reaction is carried out by combining the components in a predetermined ratio and then adding acidic or basic water to the components at a controlled rate to form silanols from the alkoxy moieties. For some end use applications of the inventive materials, a slightly higher molecular weight (higher number of silanol reactive groups) is preferred and in this case, the silicate component is treated for a short period of time by acidic or basic water to cause the silicate component to hydrolyze and condense before the other components are added.

By the preferred means, the following reaction sequence is achieved:

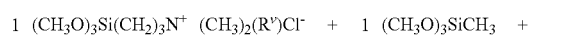

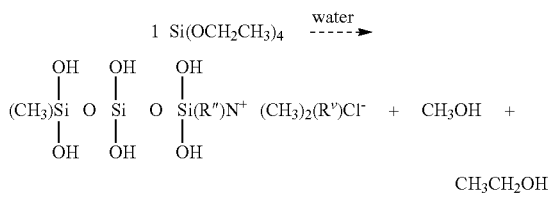

No heat is used in this reaction as higher temperatures (in excess of about 150° C. may result in a gelation of the reaction mixture. There is a small exotherm from the hydrolysis reaction but the heat is not sufficient to provide problems with the resultant product. Thus, the reaction is generally run at or near room temperature. No solvents are required in this reaction, but it is within the scope of this invention to utilize solvents. It should be noted that the byproduct of the hydrolysis reaction is alcohol. Typically, the products of this reaction do not need filtration.

As mention Supra, it is possible to enhance the molecular weight and thereby increase the amount of silanol functionality on the molecule by first mildly hydrolyzing the ortho precursor and then adding the remainder of the components.

Thus, a molecule having the following average formula may be obtained:

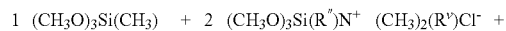

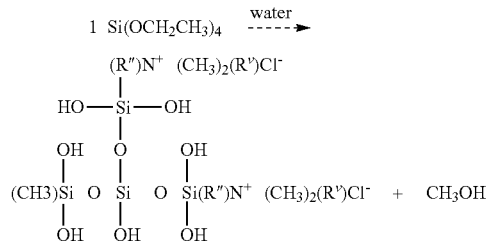

One can also provide a material having the formula:

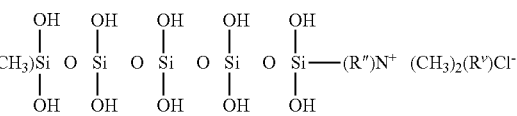

by hydrolyzing the components 1 $(CH_3O)_3Si(CH_3)$, 3 $Si(OCH_2CH_3)_4$ and 1 $(CH_3O)_3Si—(R'')N^+ (CH_3)_2(R^v)Cl^-$. A preferred material is

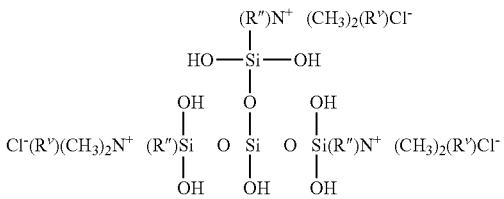

The materials are liquids as prepared. In some cases, if preferred, the by-produced alcohols and any residual water can be removed to provide a solid material, and in some cases the solid material is hard and appears to be almost crystalline and in some cases, the material is waxy or paste-like.

The materials of this invention are also suitable for providing adhesion in combination with reactive organic compounds, such as ionomers, especially glass ionomers, or urethanes.

EXAMPLES

General Processing

The tetraethylorthosilicate (TEOS) or the tetrabutyl-titanate (TBT) were placed into a 40 ml vial with a magnetic stirring bar. The functional trialkoxysilanes were added and allowed to mix for 30 minutes. Water, adjusted with KOH to pH 10 or HCl to pH 2, was added dropwise with agitation. This was allowed to hydrolyze for 60 minutes and 24 hours after which the solution was evaluated for appearance. All weights are in grams. Compound molecular weights were used to calculate the Moles and molar ratios of each component.

TABLE I shows the reaction product of the functional alkoxysilane onto a silicate surface and the resulting material. The molar ratio of functional alkoxysilane to silicate varies from 1/1/1 in example 1 to 1/10/1, example 8, with molar ratios in between these numbers. Examples 1, 2, and 2A demonstrate increasing water concentration from 10 moles to 40 moles and the resulting solutions after 24 hours and 14 days ambient aging. Samples of the solutions were placed into an aluminum cup and heated for 24 hours at 35° C. These materials resulted in a waxy solid film that could be easily dispersed in water or alcohol.

TABLE I

| | | sample# | | | | | | | | | | | |
|---|---|---|---|---|---|---|---|---|---|---|---|---|---|
| | mw | 1 | 2 | 2A | 3 | 4 | 4A | 5 | 6 | 6A | 7 | 7A | 8 |
| TEOS | 208 | 2.08 | 2.08 | 2.08 | 2.08 | 2.08 | 6.24 | 2.08 | | | 2.08 | 2.08 | 2.08 |
| TBT | 340 | | | | | | | | 3.4 | 3.4 | | | |
| MTM | 136 | 1.36 | 1.36 | 1.36 | 1.36 | 1.36 | 1.36 | | 1.36 | 1.36 | 1.36 | 1.36 | 1.36 |
| N+@42% | 496 | 11.8 | 11.8 | 11.8 | 23.6 | 11.8 | 11.8 | 35.4 | 11.8 | 11.8 | 11.8 | 11.8 | 11.8 |
| Water[1] | | 1.8 | 3.6 | 7.2 | 1.8 | 1.8 | 3.6 | 1.8 | 1.8 | 3.6 | | | 1.17 |
| Water[2] | | | | | | | | | | | 1.8 | 3.6 | |
| Mole ratio[3] | | 1/1/1 | 1/1/1 | 1/1/1 | 1/1/2 | 1/3/1 | 1/3/1 | 0/1/3 | 1/1/1 | 1/1/1 | 1/1/1 | 1/1/1 | 1/10/1 |
| Soln@24 hrs.[4] | | clear | clear | cloudy | clear | clear | cloudy | clear | clear | cloudy | clear | cloudy | clear |

TABLE I-continued

| | mw | 1 | 2 | 2A | 3 | 4 | 4A | 5 | 6 | 6A | 7 | 7A | 8 |
|---|---|---|---|---|---|---|---|---|---|---|---|---|---|
| Soln@14 days[5] | | clear | clear | 2 phase | clear | clear | clear | clear | clear | 2 phase | clear | 2 phase | 2 phase |
| Heated[6] | | waxy solid | | waxy solid | | | | waxy solid | | | | | waxy solid |

[1]pH = 10
[2]pH = 2
[3]moles M/TEOS/N+ at 42%
[4]@23°
[5]@23°
[6]@35°
MTM = methytrimethoxysilane
N+@42% = $(CH_3O)Si(R")N^+(CH_3)_2(C_{18}H_{37})Cl^-$ Biocryl resin was obtained from Great Lakes Orthodontics, Ltd. This is a two part cold cure acrylic resin and splint resin. The manufacturer's mixing technique is: 1. Mix 2 parts polymer with 2. 1 part of monomer. In a medium resin mix cup, always adding the powder to the liquid resin. Example 3 was added to the mix using the manufacturer's technique. From Table I, all of the samples cured at ambient conditions. Flexibility was evaluated after a 24 hour ambient cure by flexing a 40 mil thick by 0.5 inch wide specimen noting the degree of the flex before fracture. Examples 1 and 2 demonstrated superior flex and toughness of the resulting film versus the control film, example 7.

TABLE II

| Sample # | 1 | 2 | 3 | 7 |
|---|---|---|---|---|
| Ortho Jet Powder | 20 | 20 | 20 | 20 |
| Sample 3 from Table I | 1 | 1 | 2 | 5 |
| Ortho Jet liquid | 10 | 10 | 10 | 10 |
| % powder added | 5 | 10 | 25 | 0 |
| Cure | Exec. | Exec. | Exec. | Exec. |
| Flex | 1 | 1 | 2 | 5 |
| Toughness | 1 | 1 | 3 | 5 |

1 = most flexible
1 = highest toughness

The multi-functional acrylate of the adhesive composition is typically selected from the group of aliphatic urethane acrylates, aromatic urethane acrylates, epoxy-functional acrylates, isobutylene acrylates, and combinations thereof. In certain aspects, the multifunctional acrylate is the aliphatic urethane acrylate, such as aliphatic urethane diacrylate.

The multi-functional acrylate is typically what is referred to in the art as a "pre-polymer." Pre-polymers are typically oligomers which are formed by reacting two or more components such that the pre-polymers have excess functional groups which remain unreacted in the pre-polymers. It is to be appreciated that the multi-functional acrylate may be a monomer or may be a polymer. In addition, the multi-functional acrylate may comprise a blend of different types of multi-functional acrylates. The blend of multi-functional acrylates may comprise any combination of multi-functional acrylates which are monomeric, oligomeric, and/or polymeric.

When the multi-functional acrylate is the aliphatic urethane acrylate, the aliphatic urethane acrylate is typically formed by reacting an isocyanate and a polyol such that the aliphatic urethane acrylate formed therefrom has at least two functional groups selected from acryloxy functional groups, methacryloxy functional groups, and combinations thereof.

At least one of the isocyanate and the polyol has at least one acryloxy functional group and/or methacryloxy functional groups, and combinations thereof. At least one of the isocyanate and the polyol has at least one acryloxy functional group and/or methacryloxy functional group, which remains in the aliphatic urethane acrylate formed from reacting the isocyanate and the polyol. As designated by the term "aliphatic," the aliphatic urethane acrylate is free from aromatic groups.

The examples in table III were made by mixing the ingredients until homogeneous (typically 60 minutes at ambient temperature). This was allowed to mix for 24 hours at ambient with agitation. As set forth above, the adhesive composition further comprises an initiating agent. The initiating agent may be any initiating agent known in the art. In certain aspects, the initiating agent comprises a photoinitiating agent. Photoinitating agents are best in the art and undergo a photoreaction upon the absorption of light, which is typically in the ultraviolet spectrum, i.e., from 300 to 400 nm. The photoreaction generally forms reactive species, which may initiate or catalyze further chemical reactions. Typically, the photoreaction initiates a polymerization or polycondensation reaction. Therefore, when the adhesive composition of the present invention includes the photoinitiating agent, the adhesive flexible film may be cured by applying ultraviolet radiation to the adhesive layer formed therefrom.

The photoinitiator and synergist were added and thoroughly mixed. A thin film was applied to 1) a glass slide and 2) an aluminum panel and cured using a Sapphire Limineers by Cerinate, DenMat Holdings, LLC, Lompoc, Calif. for six seconds. The resulting film was abraded using a stainless steel spatula recording the resulting film strength. A 0.250 inch film was UV cured using a Sapphire Limineers by Cerinate for six seconds. The resulting piece was abraded using a stainless steel spatula recording the resulting strength.

The material from TABLE III, example 4 was placed between two glass slides and compressed to a film thickness of about 10 mils. This was UV cured for 6 seconds at ambient using a Sapphire Limineers by Cerinate. The glass slides could not be separated indicating a very high level of adhesion.

Sample 6 was placed between two glass slides and compressed to a film thickness of about 5 mils. These were then UV cured using a Sapphire Limineers by Cerinate for six seconds. The glass slides could not be separated indicating a very high level of adhesion.

TABLE III

| Sample # | 4 | 5 | 6 |
|---|---|---|---|
| Urethane Dimethacrylate X850 | | | 8.5 |
| Bis-GMA | 8.5 | 8.5 | |
| 1,6 hexanediol Dimethacrylate | 8.5 | 8.5 | 8.5 |
| Sample 5 | 1.7 | 3.4 | 3.4 |
| Camphorquinone | 0.2 | 0.2 | 0.2 |
| Ethyl-4-Dimethylamino benzoate | 0.2 | 0.2 | 0.2 |
| UV cure/6 sec. Glass/aluminum | hard film yellow | hard film yellow | very hard Film, yellow |
| Thick section cure (¼ inch thick) | very hard film, yellow | very hard film, yellow | very hard film, yellow |

What is claimed is:

1. A composition of matter having the average general formula:

$$(RSi)_x \quad (WO_y)_s (R'Si)_z$$

with R substituents, wherein the average molar ratio of x:y:z is 0.25-3:4:0.25-3, with the proviso that there is present at least one R'Si— unit and W is independently selected from the group consisting of Si, Ti, Zr, and, wherein R is independently selected from the group consisting essentially of hydroxyl radicals, alkyl groups of 1 to 8 carbon atoms, substituted alkyl groups of 1 to 8 carbon atoms, aryl groups, substituted aryl groups of 1 to 8 carbon atoms;

y has a value of 4;

s has an average value of 1 to 5;

R' is the group —(R")N$^+$(CH$_3$)$_2$ (R$^v$)Cl$^-$, wherein R" is an alkylene radical of three to six carbon atoms, R$^v$ is an alkyl radical of 10 to 22 carbon atoms, wherein WOy is derived from W(OR''')$_4$ wherein (OR''') is independently selected from the group consisting of —OCH$_3$, —OCH$_2$CH$_3$, —OCH(CH$_3$)$_2$, —O(CH$_2$)$_3$CH$_3$, —OCH$_2$CH(CH$_3$)$_2$, —O(2-ethylhexyl), acetoxy, and, oximo.

2. A composition of matter as claimed in claim 1 having the average formula $$(RSi)(OH)_2 —(O—Si)_s —O—(SiR')(OH)_2$$

with OH groups on each Si, wherein $s$ has an average value of from 1 to 5.

3. A composition of matter as claimed in claim 1 having the average formula

[structure with HO—Si(R')—OH bridge on middle Si]

wherein $s$ has an average value of from 1 to 5.

4. A composition of matter as claimed in claim 1 having the average formula

[structure with HO—Si(R')—OH above and O—Si—R' below middle Si]

, wherein $s$ has an average value of from 1 to 5.

5. A composition of matter as claimed in claim 1 having the average formula

[structure with R'Si—O above and O—Si—R' below middle Si]

wherein $s$ has an average value of from 1 to 5.

6. A composition of matter as claimed in claim 1 having the average formula

[structure with R'SiO groups on middle Si]

wherein $s$ has an average value of from 1 to 5.

7. A composition as claimed in claim 1 in combination with a modified glass ionomer.

8. A method of providing surfactancy to a solution, the method comprising providing a composition of claim 1 and combining said composition with water.

9. A composition of matter comprising a composition of claim 1 and an ionomer.

10. A method of providing adhesion, the method comprising providing a composition of claim 1 and combining said composition with an ionomer.

11. The method as claimed in claim 10 wherein the ionomer is a glass ionomer.

* * * * *